United States Patent [19]

Vanlerberghe et al.

[11] Patent Number: 4,584,196
[45] Date of Patent: Apr. 22, 1986

[54] PERFLUORINATED SURFACE-ACTIVE OLIGOMERS AND COMPOSITIONS FOR TREATING HAIR CONTAINING THESE OLIGOMERS

[75] Inventors: Guy Vanlerberghe, Claye-Souilly; Henri Sebag, Paris, both of France

[73] Assignee: L'Oreal, Paris, France

[21] Appl. No.: 473,639

[22] Filed: Mar. 9, 1983

Related U.S. Application Data

[62] Division of Ser. No. 156,398, Jun. 4, 1980, Pat. No. 4,399,077.

[30] Foreign Application Priority Data

Jun. 7, 1979 [FR] France .................................. 79 14639

[51] Int. Cl.$^4$ ...................... A61K 7/075; A61K 7/08; C07C 149/20; C07C 141/02; C07C 143/12; C07C 147/14
[52] U.S. Cl. .................................. 424/70; 260/501.16; 424/71; 424/72; 424/DIG. 2; 560/149; 562/581; 558/34
[58] Field of Search ................ 560/149, 151; 562/581; 564/297, 505; 568/37, 46, 615; 260/501.12, 501.13, 501.19, 501.16, 458 R; 424/DIG. 2, 70, 72, 71; 514/880, 881

[56] References Cited

U.S. PATENT DOCUMENTS

| | | | |
|---|---|---|---|
| 3,879,471 | 4/1975 | Farber | 568/46 X |
| 3,959,462 | 5/1976 | Parks et al. | 424/70 |
| 4,015,612 | 4/1977 | Pavlik et al. | 424/DIG. 2 X |
| 4,199,562 | 4/1980 | Vanlerberghe et al. | 424/70 X |
| 4,408,043 | 10/1983 | Seale et al. | 564/505 X |
| 4,430,250 | 2/1984 | Sebag et al. | 424/72 X |

Primary Examiner—Natalie Trousof
Assistant Examiner—Patricia M. Scott
Attorney, Agent, or Firm—Cushman, Darby & Cushman

[57] ABSTRACT

Perfluorinated surface-active block or random oligomers of the formula

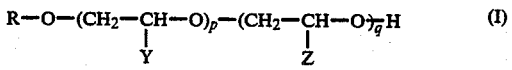

(I)

where
R denotes a $C_2$–$C_{18}$-hydrocarbon or -hydrofluorocarbon radical,
Y denotes a $C_6$–$C_{13}$-fluorocarbon or -hydrofluorocarbon radical which can contain a chain oxygen atom,
Z denotes a group which confers solubility in water and
p and q denote integers or decimal numbers from 0.5 to 30 are provided. They are suitable for use in cosmetic compositions for the treatment of hair. They slow down the flow of sebum and the rate at which hair becomes greasy again.

12 Claims, No Drawings

PERFLUORINATED SURFACE-ACTIVE OLIGOMERS AND COMPOSITIONS FOR TREATING HAIR CONTAINING THESE OLIGOMERS

This is a division of application Ser. No. 156,398, filed 6/4/80, now U.S. Pat. No. 4,399,077.

The present invention relates to perfluorinated surface-active block oligomers or random oligomers, a process for their preparation, and their use for the treatment of hair.

A large number of surface-active agents are known; they owe their surface-activity to the amphiphilic character resulting from the juxtaposition of an oleophilic or hydrophobic hydrocarbon chain and a hydrophilic part, these being balanced for the type of properties desired. These products have found numerous applications in a great diversity of fields. They possess various structures, but a limit is imposed on their properties by the nature of the hydrophobic part.

This hydrophobic part in general consists of a long-chain aliphatic hydrocarbon radical originating from fatty acids or fatty alcohols, or of an alkylaryl radical. The choice available for this hydrocarbon part is relatively limited and consequently the properties of the products obtained remain substantially of the same order.

In order to achieve novel properties, it has been proposed to replace the oleophobic hydrophobic part by a perfluoroalkyl chain which exhibits both hydrophobic and oleophobic properties. This hydrophobic and oleophobic chain is linked to a hydrophilic group which can be anionic, cationic or non-ionic.

The presence of a perfluoroalkyl chain which is both hydrophobic and oleophobic has the advantage of imparting an oleofugic effect to the substrate to which the surfactant is applied. By an "oleofugic effect" is meant the effect which tends to prevent spreading of oils and greases on the substrate.

The use of such a surfactant is of great interest in hair conditioning compositions and in particular in shampoos, and in rinses and lotions employed before or after shampooing, intended for hair which tends to be greasy.

In fact, these surfactants impart an oleofugic effect to the hair, which has the result of slowing down the rate at which the hair again becomes greasy due to sebum, and of retarding the adsorption of dirt.

It has already been proposed, especially in U.S. Pat. No. 3,959,462, to use, for hair care, compositions containing hydrofluorocarbon polymers obtained by aqueous emulsion methods.

However, it has been found that it is not possible to obtain a truly pronounced anti-grease effect with cosmetic compositions for the hair containing fluorinated polymers in emulsion.

The perfluorinated surface-active oligomers according to the present invention exhibit good surface-active properties, good solubility in water or sufficient affinity for water to be easily dispersed in an aqueous medium without it being necessary to add an emulsifier, and good oleofugic properties.

Furthermore, the perfluorinated surface-active oligomers according to the present invention have the advantage of hardly attacking the skin and the mucous membranes of the eye.

The invention provides perfluorinated surface-active products such as block oligomers and random oligomers, which can be represented by the formula:

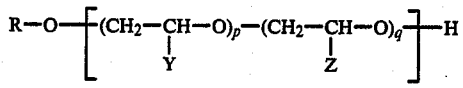 (I)

in which R denotes a straight-chain or branched hydrocarbon or hydrofluorocarbon radical having from 2 to 18 carbon atoms, or a mixture of such radicals, such as the group:

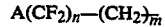

where
A denotes a hydrogen atom or fluorine atom,
m denotes an integer from 1 to 16 and
n denotes zero or an integer from 1 to 16,
with the proviso that if n denotes zero, A denotes hydrogen and if n denotes an integer from 1 to 16, m denotes the number 1, 2 or 3.

Preferably, R denotes a radical chosen from the following:

H $(CH_2)_m$—
F $(CF_2)_n$—$CH_2$—
F $(CF_2)_n$—$CH_2$—$CH_2$—
H $(CF_2)_n$—$CH_2$— which are identical or different where m and n denote an integer from 1 to 16. The group R—O—can be joined to the group

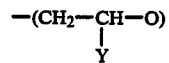

or to the group

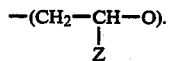

Y denotes a fluorocarbon or hydrofluorocarbon radical having from 6 to 13 carbon atoms, the hydrocarbon chain optionally containing an oxygen atom; preferably Y denotes one of the groups indicated below:
(i) $C_xF_{2x+1}$—
(ii) $C_xF_{2x+1}$—$CH_2$—
(iii) $C_xF_{2x+1}$—$CH_2$—O—$CH_2$—
(iv) $C_xF_{2x+1}$—$CH_2$—$CH_2$—O—$CH_2$—
(v) $HC_xF_{2x}$—$CH_2$—O—$CH_2$—
where x denotes an integer from 6 to 10, Z denotes an ionic or non-ionic group which confers solubility in water, and preferably one of the following groups:

(a) —$CH_2OH$ (b) 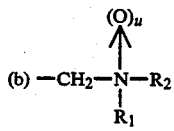

-continued (c) 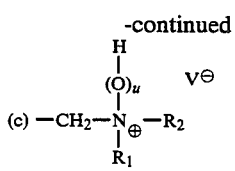

(d) 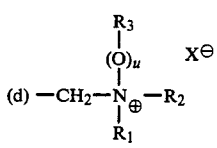

(e) 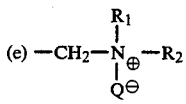

(f) 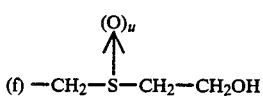

(g) 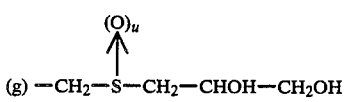

(h) 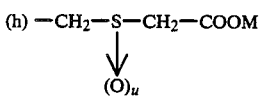

(i) —CH$_2$—O—SO$_3$M (j) —CH$_2$—O—COCH$_2$SO$_3$M where R$_1$ and R$_2$, which are identical or different, denote an alkyl or hydroxyalkyl radical having 1 or 2 carbon atoms, such as a methyl, ethyl or hydroxyethyl radical, and R$_3$ denotes an alkyl or hydroxyalkyl radical and in particular a monohydroxyalkyl or dihydroxyalkyl radical having from 1 to 3 carbon atoms, and preferably a methyl, ethyl, hydroxyethyl or dihydroxypropyl radical, and M denotes a hydrogen atom or an alkali metal or alkaline earth metal and preferably Na, K, Ca or Mg, or an ammonium group or a protonized amine group.

Suitable amines which can be used include the alkanolamines and more particularly triethanolamine, 2-amino-2-methyl-propan-1-ol and 2-amino-2-methyl-propane-1,3-diol.

Q$^\ominus$ denotes a grouping chosen from
—CH$_2$—COO$^\ominus$,
—CH$_2$—CH$_2$COO$^\ominus$,
—CH$_2$—CH$_2$—CH$_2$—SO$_3^\ominus$, V$^-$ denotes an inorganic or organic acid radical and preferably a hydrochloric, hydrobromic, sulphuric, phosphoric, acetic, lactic or tartaric acid radical, X$^-$ denotes a chloride, bromide, methylsulphate, methanesulphonate or para-toluenesulphonate anion.

u denotes 0 to 1, and p and q, which are identical or different, denote integers or decimal numbers from 0.5 to 30, with p preferably denoting a number from 0.5 to 10, more particularly from 3 to 6, and q preferably denoting a number from 3 to 20. These decimal numbers correspond to the number of moles of oxirane compound used and represent an average value for the product. It will be appreciated that, in general, a mixture will be obtained of individual compounds with different chain lengths.

The relative proportions of p and q can be adjusted depending on the desired properties.

The oleofugic character increases as p increases (the compounds at the same time acquire hydrofugic properties) and the hydrophilic character or solubility in water increases as q increases.

The sequence of units containing the groups Y and Z may be in the form of blocks, or may be random. In the former case, there is a block consisting of several units containing the group Y, joined to a second block of several units containing the group Z, and the group R—O— can be joined to one or the other of these blocks;

In the second case, the distribution of the units containing the groups Y and Z is a random distribution.

The products according to the invention can be prepared by successive or simultaneous polyaddition of reactants, containing a terminal oxirane group, with an alcohol, or mixture of alcohols, of the formula

R—OH where R has the meanings indicated above.

The reactants having a terminal oxirane group have the formulae:

 (III)

and

 (IV)

A mixture of intermediate compounds of the formula:

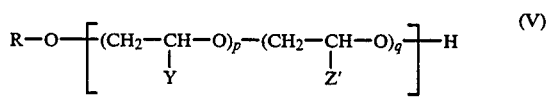 (V)

can thus be obtained.

In this formula (V), Z' denotes either the group —CH$_2$—O—C—(CH$_3$)$_3$ originating from tertiary butyl glycidyl ether, in which case the formula (V) may be written in the form (Va)

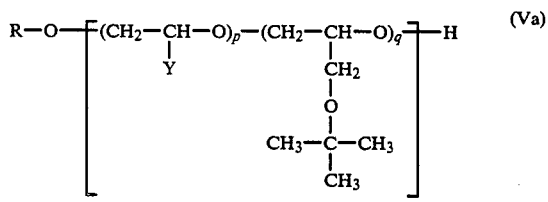 (Va)

or the group —CH$_2$Cl or —CH$_2$Br originating from epichlorohydrin or epibromohydrin, in which case formula (V) can be written in the form (Vb)

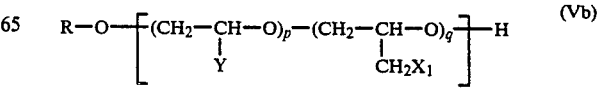 (Vb)

In the formulae (V), (Va) and (Vb) the group R—O can also be joined to the other block than that containing Y.

In the formulae (V), (Va) and (Vb)

$X_1$ denotes Cl or Br, and Y, p and q have the meanings indicated above.

As reactants of type (III) it is possible to use, with advantage, the following epoxides:

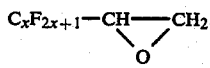    (IIIa)

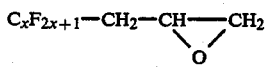    (IIIb)

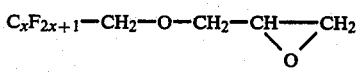    (IIIc)

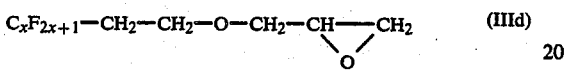    (IIId)

where x denotes an integer from 6 to 10.

The use of reactants of the type (IIIc) and (IIId), containing a hydrocarbon part and an ether bridge, makes it possible to increase the solubility of the perfluorinated surface-active oligomers in organic solvents.

This increase in the affinity for organic solvents is accompanied by a slight reduction in the oleofugic character.

The choice of the alcohol of the formula ROH, of the reactant of type (III), of the group Z and of the numbers p and q is made in accordance with the desired properties.

The polyaddition reactions of the epoxides of the formulae (III) and (IV) with the alcohols of the formula ROH are suitably carried out at a temperature from 0° to 120° C., in the presence of an acid catalyst, advantageously $BF_3$, $SnCl_4$ or $SbCl_5$. Preferably, the ether complex of $BF_3$ is used.

The epoxide compounds of the formulae (III) and (IV) are typically gradually introduced into the reactin medium, consisting of the alcohol of the formula ROH and the catalyst, the epoxides being introduced in sequence, or simultaneously.

The group Z' is subsequently converted to a water-solubilizing ionic or non-ionic group.

This conversion can be effected in accordance with known processes, the most important of which will be mentioned.

Thus, for example, the perfluorinated surface-active oligomers of type Z(a) where Z denotes the group —$CH_2OH$    (a)

can be prepared typically as follows:

(1) if Z' denotes the group

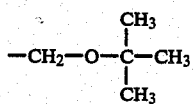

by hydrolysis in the presence of a sulphocarboxylic acid and, if appropriate, of water, at a temperature of, say, 80°–110° C.;

(2) if Z' denotes the group —$CH_2Cl$ or —$CH_2Br$ by heating at, say, 180° C.–190° C. with an alkali metal salt of a carboxylic acid and preferably with sodium acetate or potassium acetate, in a solvent which at one and the same time ensures that the reactants are miscible and that the alkali metal halide formed is easy to separate off, and preferably in the presence of a glycol such as ethylene glycol, butylene glycol, diethylene glycol or an ether thereof, propylene glycol, dipropylene glycol, hexylene glycol or 2-butoxyethanol, the acetic acid ester formed being saponified with sodium hydroxide or potassium hydroxide, or alternatively by alcoholysis with anhydrous methanol or ethanol in the presence of a catalyst which is advantageously sodium methylate or ethylate or potassium methylate or ethylate.

The perfluorinated surface-active oligomers of type Z(b), can be prepared by heating the intermediate compound of the formula (Vb) with the secondary amine of the formula:

which is generally used in excess, at, say, 100°–150° C., if appropriate in an autoclave. The excess can subsequently be removed by washing with water or by heating under reduced pressure.

Amongst the amines preferably used there may be mentioned dimethylamine, diethylamine, methylethanolamine, ethylethanolamine and dihydroxyethylamine.

If u=1, the amine compounds thus obtained can be oxidized with hydrogen peroxide at a temperature of 25° to 90° C.

The perfluorinated surface-active oligomers of type Z(c) can be prepared by neutralizing the compounds of type Z(b) with an inorganic or organic acid VH, such as hydrochloric, hydrobromic, sulphuric, phosphoric, acetic, lactic or tartaric acid.

The perfluorinated surface active oligomers of type Z(d) can be prepared by alkylation of the compounds of type Z(b) with alkylating agents such as methyl or ethyl chloride, bromide or iodide, dimethyl sulphate, methyl methanesulphonate or methyl paratoluenesulphonate, glycol chlorohydrin or glycerol chlorohydrin.

These alkylation reactions are generally carried out at a temperature of, say, 10° to 80° C., if desired in the presence of a solvent such as alcohols, aromatic solvents or inert chlorinated solvents.

The perfluorinated surface-active oligomers of type Z(e) can be prepared by alkylation of the compounds of type Z(b), in which u=0, with alkylating agents such as methyl or ethyl chloroacetate or chloropropionate, at a temperature of, say, 10° to 80° C., if desired in the presence of a solvent such as alcohols, aromatic solvents or inert chlorinated solvents, this alkylation being followed by a saponification with sodium hydroxide or potassium hydroxide.

If $Q^\ominus$ denotes —$CH_2$—$CH_2$—$CH_2SO_3^\ominus$, the alkylation should be carried out in the presence of propanesultone.

The perfluorinated surface-active oligomers of type Z(f) and Z(g) can be prepared by heating the intermediate compounds of the formula (Vb) with thioethanol or thioglycerol, in the presence of sodium or potassium methylate, ethylate or hydroxide, and of a solvent which is generally an alcohol (for example ethanol, propanol, isopropanol, butanol or tertiary butanol), an alkoxyethanol of which the alkyl group contains 1 to 4 carbon atoms, or a glycol such as ethylene glycol, propylene glycol, diethylene glycol or dipropylene glycol, if desired in the presence of water, at a temperature of, say, 60° to 120° C.

If u=1, the products can be oxidized with hydrogen peroxide at a temperature of, say, 20° to 50° C., if desired in the presence of an organic acid such as acetic acid.

The perfluorinated surface-active oligomers of type Z(h) can be prepared by reacting the intermediate compound (Vb) with ethyl thioglycolate in the presence of sodium or potassium methylate, ethylate or hydroxide and of a solvent which may be one of those indicated for the preparation of the compounds of type Z(f) and Z(g), if appropriate in the presence of water, and at a temperature of, say, 60° to 120° C.

If u=1, the products can be oxidized with hydrogen peroxide under the conditions indicated for the compounds of type Z(f) and Z(g).

After saponification, and after obtaining the acid, the reaction mixture can be washed and then neutralized, if desired, with an alkali metal hydroxide or alkaline earth metal hydroxide or with an amine, preferably an alkanolamine such as triethanolamine, 2-amino-2-methyl-propan-1-ol or 2-amino-2-methylpropane-1,3-diol.

The perfluorinated surface-active oligomers of type Z(i) can be prepared by sulphation of the compounds of type Z(a) with chlorosulphonic acid in the presence of an inert solvent, for example an aromatic or chlorinated solvent, at a temperature of, say, 0° to 50° C.

The product is then neutralized with sodium or potassium methylate, ethylate or hydroxide or with an amine, preferably an alkanolamine such as triethanolamine, 2-amino-2-methyl-propan-1-ol or 2-amino-2-methylpropane-1,3-diol.

The perfluorinated surface-active oligomers of type Z(j) can be prepared by esterification of the compounds of type Z(a) with sulphoacetic acid or by direct treatment of the intermediate products of the formula (Va) with sulphoacetic acid at a temperature of, say, 100°-140° C.

The products obtained are subsequently neutralized as indicated for the compounds of type Z(i).

The compounds according to the invention are generally soluble in water, or easily dispersible. They exhibit a very marked oleofugic character towards oils. It follows that substrates treated with perfluorinated surfactants of the formula (I) resist impregnation with oils.

The perfluorinated surface-active oligomers of the formula (I) are suitable for use in cosmetic compositions for the treatment of hair, in general in the form of aqueous or aqueous-alcoholic compositions containing, in particular, 0.02 to 5% by weight, and more particularly 0.05% to 2% by weight, of the oligomer.

The use of the aqueous or aqueous-alcoholic compositions containing the compounds of the formula (I) in the case of hair treatments imparts to the hair an oleofugic effect which manifests itself in a slowing down of the flow of sebum and in a delay in the hair becoming greasy again, and a delay in the adsorption of dirt. This oleofugic effect is in particular advantageous for hair which tends to be greasy.

This invention thus also provides compositions for the treatment of hair and in particular shampoos, lotions for use before or after shampooing, rinses, wave-setting solutions, reducing or oxidizing solutions for permanent waving, and brushing lotions, containing one or more of the oligomers.

The compositions for the treatment of hair are suitably in the form of an aqueous or aqueous-alcoholic solution or in the form of a cream, a gel, a dispersion or a powder, or can be packaged in the form of an aerosol.

The aqueous-alcoholic solutions generally contain an alcohol, preferably ethanol or isopropanol, glycol, glycol ether or mixtures of these, advantageously in a proportion of 5 to 70% of the total weight of the composition.

The compositions for the treatment of hair in general contain from 0.02 to 5% and advantageously from 0.05 to 2% of perfluorinated surface-active oligomers of the formula (I).

The cosmetic hair compositions can also contain an adjuvant, preferably an anionic, cationic, amphoteric, zwitter-ionic or non-ionic surfactant, perfume, dyestuff, preservative, thickener, foam stabilizer, softener, hair-restructuring agent, anti-dandruff agent, cosmetic resin, acidifying or alkalizing agent, opacifying agent or sequestering agent.

The present invention also provides a process for the treatment of hair which consists in applying to the hair an efficacious quantity of an aqueous or aqueous-alcoholic composition containing one or more perfluorinated surface-active oligomers of the formula (I), optionally with one or more adjuvants as defined above.

The following examples further illustrate the present invention.

EXAMPLE 1

Preparation of a mixture of random oligomers of the formula:

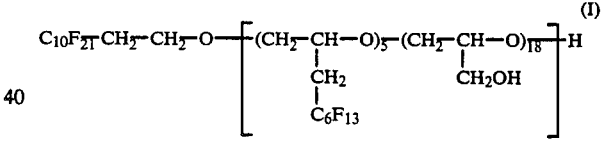

I. Preparation of the intermediate compounds of type (Va), of the formula:

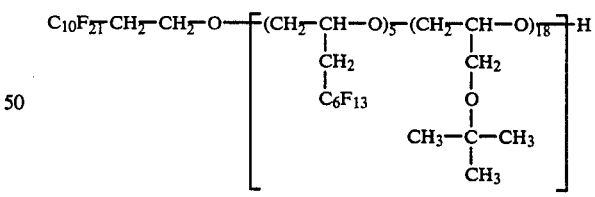

3.94 g (0.007 mol) of 1H,1H,2H,2H-perfluorododecanol are dissolved in 4 ml of diethylene glycol dimethyl ether and 0.05 ml of the ether complex of $BF_3$ is added.

Separately, a mixture of 16.4 g (0.126 mol) of tertiary butyl glycidyl ether and 13.1 g (0.035 mol) of 1H,1H,2H,3H,3H-perfluorononylene 1,2-oxide is prepared. The solution of the perfluorinated alcohol in diethylene glycol dimethyl ether is heated to 75°-80° C. and the mixture prepared above is added dropwise thereto, whilst keeping the temperature at 75°±5° C. and stirring. During the addition of the mixture, 0.05 ml of the ether complex of $BF_3$ is added 4 times. After completion of the addition, stirring is continued for 15 minutes and a determination shows that the presence of epoxide groups is no longer detectable.

The product thus obtained is washed twice with 30 ml of boiling water and then dried under reduced pressure.

The mixture of intermediate compounds of the formula indicated above is obtained in the form of a liquid which has a pale yellow color and is viscous at ambient temperature.

II. 0.15 g of sulphoacetic acid is added to 15 g of the intermediate compounds thus obtained. The mixture is gradually heated to 120° C. and is kept at this temperature for 2 hours 20 minutes. The sulphoacetic acid is neutralized in an aqueous-alcoholic medium by stirring in the presence of Amberlite MBI resin, after which the solvent is removed by distillation under reduced pressure.

This gives 10 g of random oligomers of the formula indicated above, in the form of an oily product which has a brown color and is soluble in water.

The cloud point in water is above 100° C.

Determination of the total fluorine gives a value of 35.18%–35,24%.

EXAMPLE 2

Preparation of a mixture of random oligomers of the formula:

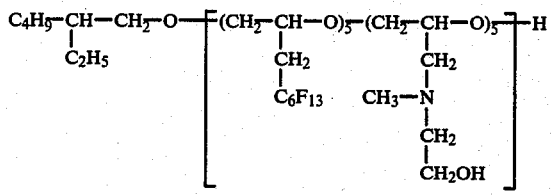

I. Preparation of the intermediate compounds of type (Vb), of the formula:

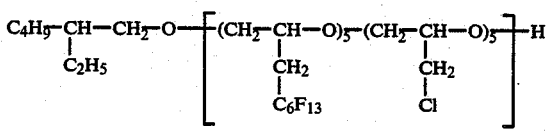

0.1 ml of the ether complex of BF$_3$ is added to 1.3 g (0.01 mol) of 2-ethylhexanol. The mixture is heated to 70° C. and a mixture composed of 18.8 g (0.05 mol) of 1H,1H,2H,3H,3H-perfluorononylene 1,2-oxide and 4.6 g (0.05) of epichlorohydrin is added dropwise whilst keeping the temperature at 70°±5° C. After completion of the addition, the mixture is kept at 75° C. for 1 hour.

A determination is carried out to confirm that the epoxide groups have disappeared.

The product thus obtained is neutralized and washed three times with its own weight of hot water, after which it is dried under reduced pressure.

II. 7 g (93 meq) of N-methylethanolamine are added to 18 g (36 meq of chlorine) of the intermediate compounds obtained above and the mixture is heated at 130° C., under a nitrogen atmosphere, for 5 hours 30 minutes.

The product thus obtained is then washed three times with its own weight of boiling water, after which it is dried under reduced pressure.

A mixture of random oligomers of the formula indicated above is obtained, which is in the form of a viscous liquid which has a light brown color, and is water-soluble in the presence of lactic acid.

Base number: 1.36 meq/g
Fluorine content: 48.6–48.3%.

EXAMPLE 3

Preparation of a mixture of block oligomers of the formula:

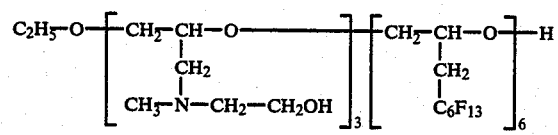

I. Preparation of the chlorinated intermediate compounds of the formula (Vb).

0.075 ml of the ether complex of BF$_3$ is added to 4.6 g (0.1 mol) of ethanol, the mixture is heated to 80° C. and 27.7 g (0.3 mol) of epichlorohydrin are then added dropwise thereto. The temperature is kept at 80° C. When the reaction ceases to be exothermic, a further 0.05 ml of the ether complex of BF$_3$ is added and the addition of epichlorohydrin is stopped.

After completion of the addition, the mixture is kept at 80° C. for a further half-hour, and a determination is carried out to confirm that the epoxide groups have disappeared.

0.05 ml of the ether complex of BF$_3$ is added to 1.94 g (0.0006 mol) of the chlorinated derivatives thus obtained, the mixture is heated to a temperature of 80° C. and 13.5 g (0.036 mol) of 1H,1H,2H,3H,3H-perfluorononylene 1,2-oxide are added dropwise whilst keeping the temperature at 80°±5° C. After completion of the addition, the mixture is kept at a temperature of 80° C. for a further 30 minutes.

II. 3 g (0.04 mol) of N-methylethanolamine and 15 ml of toluene are added to 14 g of the chlorinated intermediate compounds (0.018 equivalent of chlorine) thus obtained, and the mixture is heated under reflux for 8 hours.

The toluene is then distilled and the mixture is heated further for 4¼ hours at 145° C. The product thus obtained is washed three times with 25 to 30 ml of boiling water to remove the N-methyl-ethanolamine hydrochloride formed, and is then dried under reduced pressure.

This gives a mixture of block oligomers of the formula indicated above, which is in the form of an oil which has a light brown color, is very viscous when cold, and is soluble in water after neutralization with lactic acid.

Base number: 0.79 meq/g
Fluorine Content: 58.06–57.93%.

EXAMPLE 4

Preparation of a mixture of random oligomers of the formula:

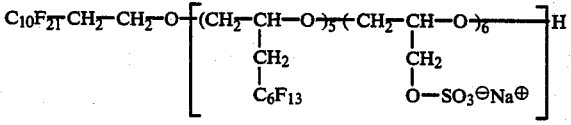

I. Preparation of the intermediate compounds of the formula (Va).

0.1 ml of the ether complex of $BF_3$ is added to 3.7 g (0.0065 mol) of 1H,1H,2H,2H-perfluorododecanol dissolved in 3.5 ml of ethylene glycol dimethyl ether.

The solution is heated to 75° C. and a mixture of 12.2 g (0.0325 mol) of 1H,1H,2H,3H,3H-perfluorononylene 1,2-oxide and 5.1 g (0.039 mol) of tertiary butyl glycidyl ether is added dropwise whilst keeping the temperature at 75°±5° C. After completion of the addition, the temperature is kept at 75° C. for 1 hour.

II. 0.17 g of sulphoacetic acid and 0.08 g of sulphopalmitic acid are added to 16.5 g of the intermediate compounds of the formula (Va) obtained above. The mixture is heated at 90°–110° C. for 4 hours.

The product thus obtained is dissolved in 30 ml of isopropanol and is neutralized by stirring with 9 g of Amberlite MBI resin. The solvent is evaporated under reduced pressure.

This gives 12.5 g of polyhydroxylic compounds which are in the form of a viscous liquid having a brown color.

OH number: 2.68 meq/g.

III. 2.4 g (0.020 mol) of chlorosulphonic acid are added slowly to 9.5 g (0.0033 mol) of the product obtained in stage II, with vigorous stirring and whilst keeping the temperature at 25° C.

The mixture is then stirred under reduced pressure for 45 minutes at 25° C. to remove the hydrochloric acid formed.

The product is then dissolved in 30 ml of ethanol and neutralized with a solution of sodium methylate in methanol.

The alcohol is distilled under reduced pressure and 13 g of a product of the above formula are obtained, the product being in the form of a water-soluble paste.

EXAMPLE 5

Preparation of a mixture of random oligomers of the formula:

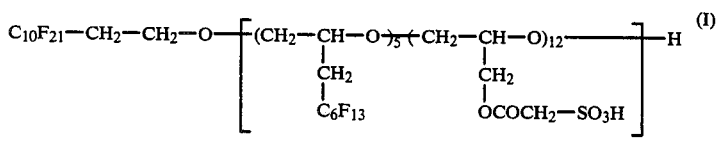

I. Preparation of the intermediate compounds of the formula (Va).

0.3 ml of the ether complex of $BF_3$ is added to 8.46 g (0.015 mol) of 1H,1H,2H,2H-perfluorododecanol dissoled in 10 g of diethylene glycol dimethyl ether, at 75° C., after which a mixture of 28.2 g (0.075 mol) of 1H,1H,2H,3H,3H-perfluorononylene 1,2-oxide and of 23.4 g (0.18 mol) of tertiary butyl glycidyl ether is added dropwise. After completion of the addition, the mixture is kept at a temperature of 80° C. for a further ½ hour.

The reaction mixture is washed with three times its own volume of water, and is then dried under reduced pressure. The intermediate compounds are thus obtained in the form of a pale yellow liquid.

II. 125 g of a solution of sulphoacetic acid in acetone, containing 2.49 meq/g (0.156 mol) of the acid, are added to 52 g (0.013 mol) of the intermediate compounds obtained above, heated to 100° C.; the acetone introduced is distilled off simultaneously, under reduced pressure, the temperature being kept at between 110° and 120° C.

The addition requires 3¾ hours. The reaction mixture is then kept for 2 hours at a temperature of 120° C. under a pressure of 30 mm Hg.

This gives a mixture of oligomers which is in the form of a product which has a black color, is solid when cold and is very viscous when hot.

Analyses

Acid number: 2.88–2.89 meq/g

Saponification number: 6.02–6.57 meq/g.

EXAMPLE 6

Preparation of a mixture of random oligomers of the formula:

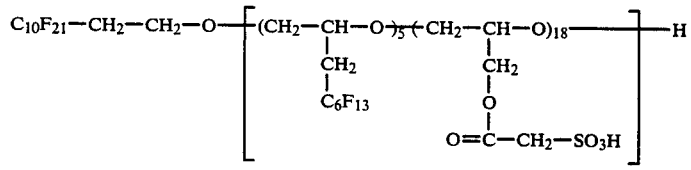

21.5 g of a solution of sulphoacetic acid in acetone (containing 3.9 meq/g of acid) are added to 12 g (0.0024 mol) of the intermediate compounds prepared in Example 1, heated to 90° C. in a water bath, the acetone being distilled off simultaneously. The temperature is in this way kept at about 75° C. for 3 hours.

15 ml of diethylene glycol dimethyl ether are then added and the temperature is raised to 100°–105° C. for 2½ hours. Thereafter the solvent is distilled under reduced pressure.

A mixture of oligomers is obtained in the form of a product which has a black color and is plastic when cold, stringy when hot, and soluble in water.

Acid number: 2.14 meg/g.

EXAMPLE 7

Preparation of a mixture of random oligomers of the formula:

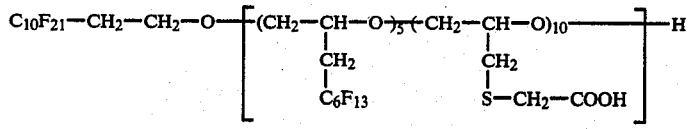

I. Preparation of the chlorinated intermediate compounds of the formula (Vb).

3.5 g of diethylene glycol dimethyl ether and 0.08 ml of the ether complex of BF$_3$ are added to 3.4 g (0.006 mol) of 1H,1H,2H,2H-perfluorododecanol. The mixture is heated to a temperature of 75° C. and a mixture of 5.6 g (0.06 mol) of epichlorohydrin and 11.3 g (0.03 mol) of 1H,1H,2H,3H,3H-perfluorononylene 1,2-oxide is added dropwise whilst keeping the temperature at 80° C.

The product obtained is then washed three times with its own weight of boiling water and is dried under reduced pressure.

II. 5.4 g (0.045 mol) of ethyl thioglycolate are added to 15.2 g (0.0045 mol) of the intermediate compounds of the formula (Vb), obtained in stage I. The mixture is heated to 70° C. and 9.4 g of a solution of sodium methylate in methanol (containing 4.8 meq/g, and hence corresponding to a total of 45 meq) are added thereto, followed by 20 ml of absolute ethanol.

The solution is heated under reflux for 6 hours, after which it is filtered and the alcohol is distilled under reduced pressure.

14.5 g (30 meq of ester groups) of the product thus obtained are dissolved in ethanol and 3 ml of an NaOH solution, containing 10 meq/g, are added.

The mixture is heated under reflux for 1 hour and is then acidified with concentrated hydrochloric acid.

The product thus obtained is washed three times with its own weight of hot water and is then dehydrated under reduced pressure.

The mixture of oligomers is in the form of a viscous oil which has a brown color and is soluble in water after neutralization with triethanolamine.

Acid number: 1.50–1.60 meq/g
Determination of total fluorine: 48%.

EXAMPLE 8

Preparation of a mixture of random oligomers of the formula:

The solution of the perfluorinated alcohol is heated to 60° C. and the mixture of epoxides is added dropwise, whilst keeping the temperature at 60°±5° C.

The mixture is heated at 60° C. for a further 30 minutes after completion of the addition, and a determination is carried out to confirm that all the epoxide has been consumed.

The product is then washed with hot water, after which it is dehydrated under reduced pressure.

II. 13.7 g (0.114 mol) of ethyl thioglycolate and 50 g of absolute ethanol are added to 42.7 g (0.019 mol) of the chlorinated derivatives prepared above. The mixture is heated at 80° C. and 19.5 g of a solution of sodium methylate in methanol, containing 5.85 meq/g (corresponding to a total of 114 meq) are added dropwise thereto.

The mixture is kept under reflux for 3 hours and is then filtered to remove the precipitate. 13 g of 40% strength sodium hydroxide solution are added to the filtrate, which is then kept for 1 hour at 50° C. and is acidified with concentrated hydrochloric acid until it gives a clearly acid reaction. It is concentrated under reduced pressure and 70 ml of hot water are then added. The organic phase thus obtained is separated off and is washed with 50 ml of boiling water and dried under reduced pressure.

A product which is in the form of a liquid having a reddish brown color is obtained.

Thioether number: 1.03 meq/g
Acid number: 1.33 meq/g (milliequivalents/gram).

III. 2.7 ml of hydrogen peroxide of 180 volumes strength (43 meq) are added to 32 g of the mixture of random oligomers obtained above (43 meq of thioether groups), at a temperature of 30° C.

The mixture is left to stand for three days at ambient temperature after which the product is dispersed in 40 ml of water and the amount of normal NaOH solution required to neutralize the acid groups, and where appropriate to saponify the ester groups, is added with stirring.

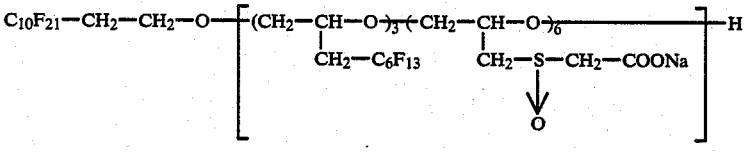

I. Preparation of the chlorinated intermediate compounds of the formula (Vb).

11.3 g (0.02 mol) of 1H,1H,2H,2H-perfluorododecanol are dissolved in 10 g of ethylene glycol dimethyl ether and 0.13 ml of the ether complex of BF$_3$ is added thereto.

Separately, a mixture of 22.5 g (0.06 mol) of 1H,1H,2H,3H,3H-perfluorononylene 1,2-oxide and 11.1 g (0.12 mol) of epichlorohydrin is prepared.

The random oligomers of the formula given above are thus obtained in the form of a limpid solution which has a pH of 7.2 and contains 16% of active matter.

EXAMPLE 9

Preparation of a mixture of random oligomers of the formula:

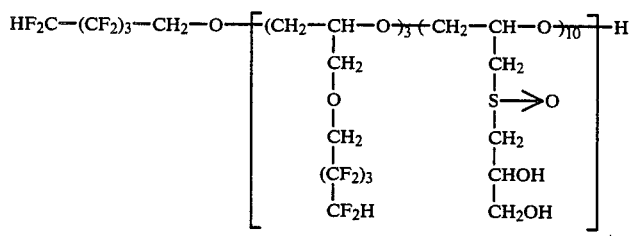

I. 0.12 ml of the ether complex of BF₃ are added to 30.2 g (0.13 mmole) of 1H, 1H, 5H-octafluoro-pentan-1-ol followed by the addition, drop by drop, of 18 g (0.196 mmole) of epichlorhydrin at 55° C. A determination shows that the presence of epoxide groups is no longer detectable.

20 g tertiobutanol are added to the above mixture at 60° C. followed by the addition, drop by drop, of 13.9 g of NaOH solution at 10 meq/g (corresponding to 139 meq). The temperature of 60° C. is maintained during 1 hour.

The mixture is washed twice with water and the organic phase is dryed on sodium sulfate. The remaining tertiobutanol is eliminated by heating at reduced pressure and the epoxide formed is distiled, at a temperature of 65°–69° C. and at a pression of 38 mmHg. Analysis shows an epoxide content of 2.40 meq/g.

II. 0.007 ml of the ether complex of BF₃ are added to 0.26 g (1.12 mmole) of 1H, 1H, 5H-octafluoro-pentan-1-ol followed by the addition at 55° C., drop by drop, of a mixture containing 1.4 g (3.36 meq) of the epoxide obtained previously and 1.04 (11.2 meq) of epichlorhydrin.

The mixture is maintained during 1 hour at the temperature of 55° C.

III. 5 g absolute ethanol (without water) are added to the above mixture, followed by the addition, drop by drop, of 1.33 g (11.2 meq) of thioglycerol, followed by the addition, at 70° C., of 1.9 g of a solution of sodium methylate containing 5.9 meq/g (corresponding to a total of 11.2 meq).

The mixture is maintained during 6 hours at 70° C.; sodium chloride is separated by filtration. The alcohol is eliminated by heating at reduced pressure. A brown colored paste is obtained.

IV. 10 g of absolute ethanol are added to 3 g (1.1 mmole) of the above product followed, at 45° C., by the addition, drop by drop, of 0.62 ml (11 mmole) of hydrogen peroxide at 200 volumes (60%). The temperature of the mixture is maintained during 2 and half hours at 45° C. The alcohol is eliminated by heating at reduced pressure and a very viscous paste having a light yellow color, which is soluble in water is obtained. Cloud point in distilled water 70° C.

EXAMPLE 10

Preparation of the lactic acid salt of the product prepared in Example 2.

0.51 g lactic acid 6.9 meq/g (corresponding to 3.5 meq of lactic acid) are added under vigorous stirring to 2 g (0.7 mmol) of product prepared in Example 2.

A soft yellow colored paste is obtained having the formula:

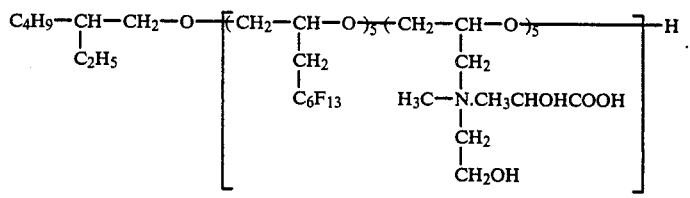

EXAMPLE A1

Non-ionic shampoo

| | |
|---|---|
| Compound of Example 1 | 0.4 g |
| Adipic acid/dimethylamino-hydroxypropyl-diethylenetriamine copolymer, sold under the registered trademark "CARTARETINE F4" by SANDOZ | 0.6 g A.M. (active matter) |
| Lauryl alcohol oxyethylneated with 12.5 mols of ethylene oxide | 10.0 g |
| Lactic acid q.s.p. pH 8 | |
| Water q.s.p. | 100 g |

EXAMPLE A2

Non-ionic shampoo

| | |
|---|---|
| Compound of Example 2 | 0.6 g |
| Vinyl acetate/crotonic acid/vinyl neodecanoate terpolymer, sold under the registered trademark "Resin 28.29.30" by NATIONAL STARCH | 0.4 g A.M. (active matter) |
| Non-ionic surfactant of the formula: R—CHOH—CH₂O—(CH₂—CHOH—CH₂—O)ₙH where R = C₉-C₁₂—alkyl and n denotes a statistical value 3.5 | 10.0 g A.M. |
| Triethanolamine, q.s.p. pH 8.9 | |
| Water, q.s.p. | 100 g |

EXAMPLE A3

Non-ionic shampoo

| | |
|---|---|
| Compound of Example 5 | 0.4 g |

-continued

| | |
|---|---|
| Polymer obtained by polycondensation of equimolecular amounts of adipic acid and of diethylenetriamine and crosslinking with 11 mols of epichlorohydrin per 100 amine groups | 0.5 g A.M. |
| Non-ionic surfactant of the formula: R—CHOH—CH$_2$O—(CH$_2$CHOH—CH$_2$—O)$_{\overline{n}}$H where R = C$_9$-C$_{12}$—alkyl and n denotes a statistical value of 3.5 | 10.0 g A.M. |
| NaOH, q.s.p. pH 7 | |
| Water, q.s.p. | 100 g |

EXAMPLE A4

Non-ionic shampoo

| | |
|---|---|
| Compound of Example 5 | 0.4 g |
| Cationic polymer comprising the unit: | 0.5 g A.M. |

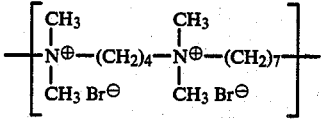

| | |
|---|---|
| Non-ionic surfactant of the formula: R—CHOH—CH$_2$O—(CH$_2$—CHOH—CH$_2$—O)$_{\overline{n}}$H where R = C$_9$-C$_{12}$—alkyl and n denotes a statistical value of 3.5 | 10.0 g A.M. |
| NaOH, q.s.p. pH 7 | |
| Water, q.s.p. | 100 g |

EXAMPLE A5

Non-ionic shampoo

| | |
|---|---|
| Compound of Example 5 | 0.4 g |
| Quaternary copolymer of vinylpyrrolidone and di(lower alkyl)-aminoalkyl acrylate, having a molecular weight of about 1,000,000, and sold under the trademark "GAFQUAT 755" by GENERAL ANILINE | 0.5 g A.M. |
| Non-ionic surfactant of the formula: R—CHOH—CH$_2$O—(CH$_2$—CHOH—CH$_2$—O)$_{\overline{n}}$H where R = C$_9$-C$_{12}$—alkyl and n denotes a statistical value of 3.5 | 10.0 g A.M. |
| NaOH, q.s.p. pH 7 | |
| Water, q.s.p. | 100 g |

EXAMPLE A6

| | |
|---|---|
| Compound of Example 6 | 0.4 g |
| Polymer obtained by polycondensation of equimolecular amounts of adipic acid and of diethylenetriamine, and crosslinking with 11 mols of epichlorohydrin per 100 amine groups | 0.5 g A.M. |
| Non-ionic surfactant of the formula: R—CHOH—CH$_2$O—(CH$_2$—CHOH—CH$_2$—O)$_{\overline{n}}$H where R = C$_9$-C$_{12}$—alkyl and n denotes a statistical value of 3.5 | 10.0 g A.M. |
| NaOH, q.s.p. pH 6.9 | |
| Water, q.s.p. | 100 g |

EXAMPLE A7

Non-ionic shampoo

| | |
|---|---|
| Compound of Example 6 | 0.5 g |
| Cationic polymer comprising the unit: | 0.4 g A.M. |

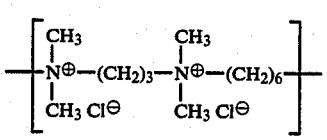

| | |
|---|---|
| Lauryl alcohol oxyethyleneated with 12.5 mols of ethylene oxide | 10.0 g |
| NaOH, q.s.p. pH 7.7 | |
| Water, q.s.p. | 100 g |

EXAMPLE A8

Anionic shampoo

| | |
|---|---|
| Compound of Example 1 | 0.5 g |
| C$_{12}$-C$_{18}$—Alkyl-dimethyl-carboxymethyl-ammonium hydroxide, sold under the registered trademark "DEHYTON AB30" by HENKEL | 3.6 g A.M. |
| Sodium lauryl-sulphate oxyethyleneated with 2.2 mols of ethylene oxide | 2.6 g |
| Lactic acid, q.s.p. pH 5 | |
| Water, q.s.p. | 100 g |

The shampoos of Examples A1 to A8 are applied to a previously wetted head of hair which tends to be greasy, and the hair is massaged so as to emulsify all the dirt. The hair is rinsed copiously with water. Shampoo is applied a second time and is left for a few moments before rinsing. The hair washed in this way is soft and glossy, and its tendency to become greasy is slowed down.

EXAMPLE A9

Rinse

| | |
|---|---|
| Compound of Example 1 | 0.5 g |
| Quaternary copolymer of vinylpyrrolidone and di(lower alkyl)-aminoalkyl acrylate, having a molecular weight of about 1,000,000, and sold under the trademark "GAFQUAT 755" by GENERAL ANILINE | 0.3 g A.M. |
| Trimethyl-cetyl-ammonium bromide | 0.2 g |
| Lactic acid, q.s.p. pH 6 | |
| Water, q.s.p. | 100 g |

This composition is applied to a clean and moist head of hair and is left thereon for a few minutes, after which the hair is rinsed and dried. The hair is soft and does not tend to become greasy again, even after several days.

EXAMPLE A10

Lotion

| | |
|---|---|
| Compound of Example 2 | 0.25 g |
| Trimethyl-cetyl-ammonium bromide | 0.20 g |
| Ethyl alcohol, q.s.p. 40° strength | |
| Lactic acid, q.s.p. pH 5 | |
| Water, q.s.p. | 100 g |

EXAMPLE A11

Lotion

| | |
|---|---|
| Compound of Example 3 | 0.25 g |
| Quaternary copolymer of vinylpyrrolidone and di(lower alkyl)-aminoalkyl acrylate, having a molecular weight of about 1,000,000 and sold under the trademark "GAFQUAT 755" by GENERAL ANILINE | 0.2 g A.M. |
| Ethyl alcohol, q.s.p. 50° strength | |
| Lactic acid, q.s.p. pH 5.5 | |
| Water, q.s.p. | 100 g |

Lotion A10 or A11 is applied to a clean and moist head of hair. After drying, the hair is soft and its tendency to become greasy is slowed down.

During the preparation of compounds of formula (I) the terminal oxirane group of the reactants of formula (III) and (IV) splits mostly in the way giving rise to groups

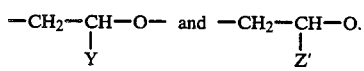

However the oxirane ring of reactants (III) and (IV) may also split in an other way, giving rise to the groups

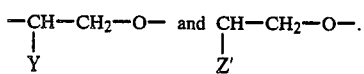

It results that the mixture of block or random oligomers of formula:

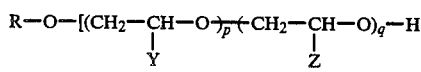 (I)

may also contain isomers of formulae:

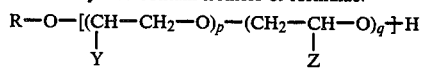 (Ia)

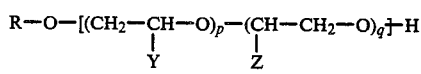 (Ib)

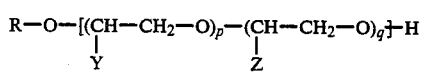 (Ic)

as well as isomers corresponding to the formulae:

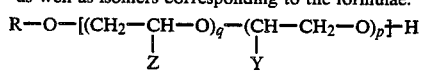 (IA bis)

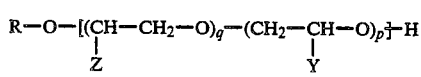 (IB bis)

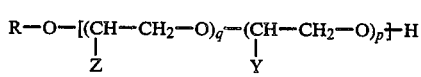 (IC bis)

We claim:

1. A perfluorinated surface-active oligomer having the formula

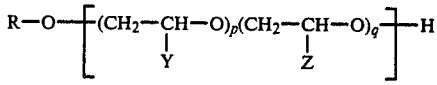

wherein
R—O— is joined to the

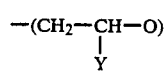

group or to the

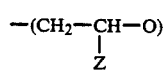

group and wherein R represents (i) a straight or branched chain hydrofluorocarbon having 2–18 carbon atoms, (ii) a straight or branched chain hydrocarbon radical having 2–18 carbon atoms, or (iii) a mixture of (i) and (ii), Y represents a fluorocarbon radical having 6 to 13 carbon atoms or a hydrofluorocarbon radical having 6 to 13 carbon atoms wherein the hydrocarbon moiety thereof optionally contains one chain oxygen atom, Z represents

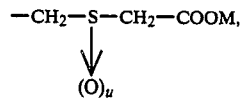

—CH$_2$—O—SO$_3$M  or  —CH$_2$—O—COCH$_2$SO$_3$M, wherein M represents hydrogen, alkali metal, alkaline earth metal, ammonium or a protonized amine selected from the group consisting of triethanolamine, 2-amino-2-methyl propan-1-ol and 2-amino-2-methyl propane-1,3-diol, p and q, each independently, represent an integer or decimal number ranging from 0.5 to 30 and u represents 0 or 1.

2. A perfluorinated surface-active oligomer having the formula

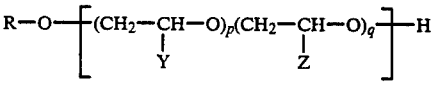

wherein R—O— is joined to the

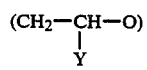

group or to the

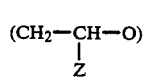

group and wherein
R represents a straight or branched chain hydrofluorocarbon having 2–18 carbon atoms, Y represents a hydrofluorocarbon radical having 6–13 carbon atoms, Z represents —CH$_2$—O—COCH$_2$SO$_3$M wherein M represents hydrogen, alkali metal, alkaline earth metal or an ammonium group, and p and q, each independently, represent an integer or decimal number ranging from 0.5 to 30.

3. The perfluorinated surface-active oligomer of claim 1 wherein R is F(CF$_2$)$_n$—CH$_2$—, F(CF$_2$)$_n$—CH$_2$—CH$_2$— or H(CF$_2$)$_n$—CH$_2$— wherein n represents an integer from 1 to 16.

4. The perfluorinated surface-active oligomer of claim 1 wherein Y is C$_x$F$_{2x+1}$—, C$_x$F$_{2x+1}$—CH$_2$—, C$_x$F$_{2x+1}$—CH$_2$—O—CH$_2$—, C$_x$F$_{2x+1}$—CH$_2$—CH$_2$—O—CH$_2$— or HC$_x$F$_{2x}$—CH$_2$—O—CH$_2$—, wherein x denotes an integer from 6 to 10.

5. The perfluorinated surface-active oligomer of claim 4 wherein Y is —CH$_2$—C$_6$F$_{13}$ or —CH$_2$—O—CH$_2$—(CF$_2$)$_3$—CF$_2$H.

6. A perfluorinated surface-active oligomer having the formula

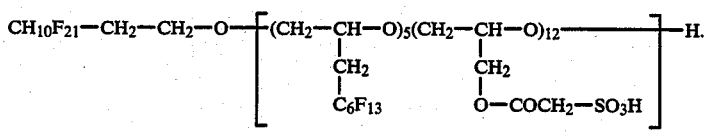

7. A perfluorinated surface-active oligomer having the formula

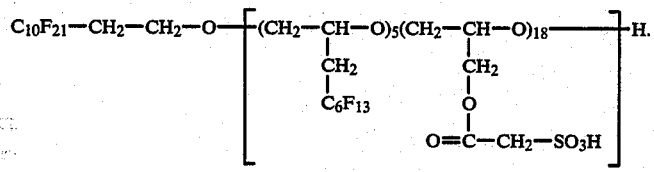

8. A shampoo, conditioning rinse or conditioning lotion composition for the hair comprising in an aqueous or aqueous-alcoholic vehicle a perfluorinated surface active oligomer in an amount effective to impart an oleofugic effect to said hair, said perfluorinated surface-active agent having the formula

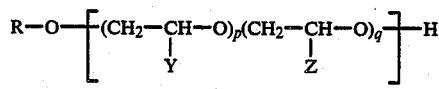

wherein R—O— is joined to the

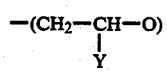

group or to the

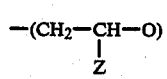

group and wherein
R represents (i) a straight or branched chain hydrofluorocarbon having 2–18 carbon atoms, (ii) a straight or branched chain hydrocarbon radical having 2–18 carbon atoms, or (iii) a mixture of (i) and (ii), Y represents a fluorcarbon radical having 6 to 13 carbon atoms or a hydrofluorocarbon radical having 6–13 carbon atoms wherein the hydrocarbon moiety thereof optionally contains one chain oxygen atom, Z represents

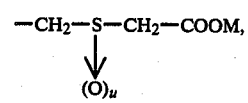

—CH$_2$—O—SO$_3$M or —CH$_2$—O—COCH$_2$SO$_3$M, wherein M represents hydrogen, alkali metal, alkaline earth metal, ammonium or a protonized amine selected from the group consisting of triethanolamine, 2-amino-2-methyl propan-1-ol and 2-amino-2-methyl propane-1,3 diol, p and q, each independently, represent an integer or decimal number ranging from 0.5 to 30 and u represents 0 or 1.

9. A shampoo, conditioning rinse or conditioning lotion composition for the hair comprising in an aqueous or aqueous-alcoholic vehicle a perfluorinated surface-active oligomer in an amount effective to impart an oleofugic effect to said hair, said perfluorinated surface-active agent having the formula

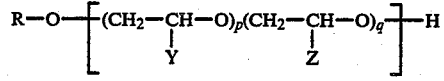

wherein R—O— is joined to the

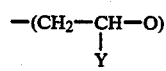

group or to the

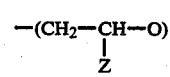

group and wherein
R represents a straight or branched chain hydrofluorocarbon having 2–18 carbon atoms,
Y represents a hydrofluorocarbon radical having 6–13 carbon atoms, Z represents —CH$_2$—O—COCH$_2$SO$_3$M wherein M represents hydrogen, alkali metal, alkaline earth metal or an ammonium group, and p and q, each independently, represent an integer or decimal number ranging from 0.5 to 30.

10. A composition of claim 8 wherein said vehicle is water, a lower alcohol, glycol or a glycol ether.

11. A composition of claim 8 which also includes an effective amount of one or more of an anionic, cationic, amphoteric, zwitterionic or nonionic surfactant; a perfume; a preservative; a thickener; a foam stabilizer; a softener; a hair restructuring agent; a cosmetic resin; an acidifying agent; an alkalizing agent; an opacifying agent; or a sequestering agent.

12. A process for imparting an oleofugic effect to hair comprising applying to said hair an effective amount of a composition of claim 8.

* * * * *